(12) United States Patent
Bailey

(10) Patent No.: US 11,879,897 B2
(45) Date of Patent: Jan. 23, 2024

(54) OPERATING A MASS SPECTROMETER UTILIZING MASS SPECTRAL DATABASE SEARCH

(71) Applicant: Thermo Finnigan LLC, San Jose, CA (US)

(72) Inventor: Derek J. Bailey, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 1061 days.

(21) Appl. No.: 16/426,929

(22) Filed: May 30, 2019

(65) Prior Publication Data

US 2020/0378983 A1     Dec. 3, 2020

(51) Int. Cl.
| | |
|---|---|
| G01N 33/68 | (2006.01) |
| H01J 49/04 | (2006.01) |
| H01J 49/42 | (2006.01) |
| H01J 49/00 | (2006.01) |

(52) U.S. Cl.
CPC ...... *G01N 33/6848* (2013.01); *H01J 49/0036* (2013.01); *H01J 49/0409* (2013.01); *H01J 49/4295* (2013.01)

(58) Field of Classification Search
CPC .............. G01N 33/6848; H01J 49/0036; H01J 49/0409; H01J 49/4295; H01J 49/0045
See application file for complete search history.

(56) References Cited

U.S. PATENT DOCUMENTS

| | | | |
|---|---|---|---|
| 7,462,354 B2 * | 12/2008 | Sette | A61K 39/29 424/192.1 |
| 7,473,892 B2 | 1/2009 | Sano et al. | |
| 7,498,568 B2 * | 3/2009 | Overney | H01J 49/004 250/281 |
| 8,168,943 B2 | 5/2012 | Schwartz et al. | |
| 10,557,837 B2 | 2/2020 | Kageyama et al. | |
| 2007/0048330 A1 * | 3/2007 | Sette | A61K 39/12 435/456 |
| 2010/0288917 A1 | 11/2010 | Satulovsky et al. | |
| 2016/0254129 A1 | 9/2016 | Richardson et al. | |

FOREIGN PATENT DOCUMENTS

| | | | |
|---|---|---|---|
| EP | 1717586 A1 | 11/2006 | |
| WO | WO-2015159096 A1 * | 10/2015 | ........... G01N 27/622 |

OTHER PUBLICATIONS

Erickson et al., "Active Instrument Engagement Combined with a Real-Time Database Search for Improved Performance of Sample Multiplexing Workflows", J. Proteome Res. 2019, 18, 1299-1306 (Year: 2019).*

(Continued)

*Primary Examiner* — David E Smith

(57) ABSTRACT

Real-time search (RTS) for mass spectrometry is described. In one aspect, a mass spectrometer can identify a candidate peptide for a product ion spectrum by searching a mass spectral database. While executing the search of the mass spectral database, the elapsed search time can be monitored. If the elapsed search time of the identification of the candidate peptide is completed before reaching a maximum value, then the mass spectrometer can perform further actions.

23 Claims, 9 Drawing Sheets

(56) References Cited

OTHER PUBLICATIONS

Erickson et al., "Active Instrument Engagement Combined with a Real-Time Database Search for Improved Performance of Sample Multiplexing Windows", J. Proteome Res. 2019, 18, 1299-1306 (Year: 2019).*

Graumann J, et al., "A Framework for Intelligent Data Acquisition and Real-Time Database Searching for Shotgun Proteomics*," Molecular & Cellular Proteomics, 2012, vol. 13, No. 3, M111. 013185, 11 pages.

Rudomin E.L, et al., "Directed sample interrogation utilizing an accurate mass exclusion-based data-dependent acquisition strategy (AMEx)," J Proteome Res., Jun. 2009, vol. 8, No. 6, pp. 3154-3160.

Schwudke D, et al., "Shotgun Lipidomics by Tandem Mass Spectrometry under Data-Dependent Acquisition Control," Methods in Enzymology, 2007, vol. 433, pp. 175-191.

Yokosuka T, et al., "'Information-Based-Acquisition' (IBA) technique with an ion-trap/time-of-flight mass spectrometer for high-throughput and reliable protein profiling," Rapid Communications in Mass Spectrometry, 2006, vol. 20, No. 17, pp. 2589-2595.

Erickson et al. "Active Instrument Engagement Combined with a Real-Time Database Search for Improved Performance of Sample Multiplexing Workflows," Journal of Proteome Research, Mar. 21, 2019, vol. 18, No. 3, pp. 1299-1306.

Anonymous, "Real-time Computing—Wikipedia", Wikipedia, Retrieved on Jun. 27, 2017.

EP Extended Search Report dated Sep. 29, 2020, to EP Patent Application No. 20167408.2.

Erickson et al., "Active Instrument Engagement Combined with a Real-Time Database Search for Improved Performance of Sample Multiplexing Workflows", J. Proteome Research, vol. 18, pp. 1299-1306 (2019).

McAlister et al., "MultiNotch MS3 Enables Accurate, Sensitive and Multiplexed Detection of Differential Expression Across Cancer Cell Line Proteomes", Analytical Chemistry, vol. 86, pp. 7150-7158 (2014).

* cited by examiner

OPERATING A MASS SPECTROMETER UTILIZING MASS SPECTRAL DATABASE SEARCH

TECHNICAL FIELD

This disclosure relates to apparatus and methods for mass spectrometry, and more particularly to data-dependent operation of a mass spectrometer using results of a mass spectral database search.

BACKGROUND

A current focus of biological mass spectrometry is the identification, quantification, and structural elucidation of peptides, proteins, and related molecules. In such experiments, it is often necessary or desirable to perform controlled fragmentation of certain ions (referred to as tandem or MSn mass spectrometry) to yield product ions, whose mass spectra provides information that may be highly useful to confirm identification or to derive structural details regarding analytes of interest. One commonly used method for MSn mass spectrometry is called data-dependent acquisition (DDA, alternatively referred to as information-dependent acquisition). The DDA technique utilizes data acquired in one mass analysis scan to automatically select, based on predetermined criteria, one or more ion species for mass isolation and fragmentation. For example, the mass spectrometer may be configured to perform a full MS (precursor ion) scan, and then select one or more ion species from the resulting spectra for subsequent MSn analysis scans based on criteria such as intensity, charge state, mass-to-charge ratio (m/z), inclusion/exclusion lists, or isotopic patterns. The DDA technique provides benefits of simplifying product ion spectra (by selecting only certain ion species for fragmentation, thereby avoiding the need to deconvolute complex product ion spectra comprising product ions produced from disparate precursor ions), and making efficient use of instrument time (by excluding from MSn analysis ions that do not meet the predetermined criteria and hence may not be of interest to the researcher).

Peptide identification is typically performed by searching the experimentally-acquired mass spectra against a mass spectral database comprising theoretical mass spectra calculated from known peptide amino acid or genetic sequences, or an empirical library of previously acquired and curated spectra. Historically, database searching is performed post-acquisition, i.e., after all of the analysis scans have been completed. More recently (see, e.g., Erickson et al., "Active Instrument Engagement Combined with a Real-Time Database Search for Improved Performance of Sample Multiplexing Workflows", J. Proteome Research, vol. 18, pp. 1299-1306 (2019), the disclosure of which is incorporated herein by reference), improved search algorithms and more powerful processors have enabled the implementation of real-time search (RTS) of mass spectral databases, in which an experimental mass spectra can be rapidly searched against a mass spectral database and one or more peptide ions present in the spectra can be identified (at least tentatively) within a time that is short relative to the duration of the presence of ion species within the mass spectrometer (e.g., the duration of a chromatographic elution peak). Using RTS, data-dependent acquisition can be performed based on criteria involving the identification of peptide ions in the spectra. This technique may be particularly valuable within the context of proteomics experiments where samples contain a complex mixture of peptides of interest and other molecules (e.g., matrix-derived substances, as well as high-abundant species that may not be of interest), allowing the researcher to increase the instrument scan time spent on MSn analysis of biologically significant peptides).

RTS must be performed quickly to increase the throughput of the mass spectrometer for increasingly complex proteomics. This is because the availability of the peptide for analysis might be relatively brief as the peptide is introduced into the mass spectrometer. If the RTS takes a significant amount of time, then the number of scans that can be performed is reduced, resulting in lower throughput, fewer data points collected, and samples wasted.

SUMMARY

One innovative aspect of the subject matter described in this disclosure includes a method of operating a mass spectrometer to analyze a biological sample. The method includes introducing peptide ions generated from the biological sample into the mass spectrometer during an introduction period; fragmenting the peptide ions to form product ions; mass analyzing the product ions to acquire a product ion spectrum; and during the introduction period, using a programmed controller to perform: executing a search of a mass spectral database to attempt to identify a candidate peptide in the mass spectral database that matches the product ion spectrum, the mass spectral database containing product mass spectral information for candidate peptides, while executing the search of the mass spectral database, monitoring an elapsed search time, and upon identification of the candidate peptide that matches the product ion spectrum prior to the elapsed search time reaching a first maximum value, causing the mass spectrometer to perform an action based on the identification.

In some implementations, introducing peptide ions includes ionizing a chromatographically separated component of the biological sample, the introduction period being defined by a chromatographic elution peak width of the component.

In some implementations, the first maximum value is defined by a user.

In some implementations, the first maximum value is defined based on a history of search results for candidate peptides not being identified before corresponding elapsed search times reached a second maximum value, the second maximum value less than the first maximum value.

In some implementations, fragmenting the peptide ions includes mass isolating at least one ion species prior to fragmentation.

In some implementations, the first maximum value is less than or equal to 20 milliseconds (ms).

In some implementations, the candidate peptide is identified using amino acid sequences stored in the mass spectral database.

In some implementations, the candidate peptide is identified using empirically determined mass spectra stored in the mass spectral database.

In some implementations, the action to be performed based on the identification of the candidate peptide includes performing an additional stage of MSn analysis for one or more of the product ion species.

In some implementations, the action to be performed based on the identification of the candidate peptide includes refraining from performing an additional stage of MSn analysis for one or more of the product ion species.

In some implementations, the action to be performed based on the identification of the candidate peptide includes adjusting a fragmentation technique implemented by a fragmentation cell used to fragment the peptide ions from a first fragmentation type to a second fragmentation type, the first fragmentation type and the second fragmentation type being different fragmentation types.

In some implementations, the method includes fragmenting the peptide ions to form second product ions; mass analyzing the second product ions to acquire a second product ion spectrum; and during the introduction period, using the programmed controller to perform: executing a second search of the mass spectral database to attempt to identify a candidate peptide in the mass spectral database that matches the second product ion spectrum, while executing the search of the mass spectral database, monitoring a second elapsed search time of the second search and determining that the second elapsed search time exceeds the first maximum value, and upon identification of the second elapsed search time exceeding the first maximum value, terminating the second search.

Another innovative aspect of the subject matter described in this disclosure includes an apparatus for analyzing a biological sample. The apparatus includes: a separation device configured to temporally separate the biological sample into components; an ionization source configured to receive a component of the biological sample and generate peptide ions from the component during an introduction period; a fragmentation device configured to fragment the peptide ions to form product ions; a mass analyzer configured to analyze the product ions to produce a product ion spectrum; and a controller programmed with instructions for: executing a search of a mass spectral database to attempt to identify a candidate peptide in the mass spectral database that matches the product ion spectrum, the mass spectral database containing product mass spectral information for candidate peptides, while executing the search of the mass spectral database, monitoring an elapsed search time, and upon identification of the candidate peptide that matches the product ion spectrum prior to the elapsed search time reaching a first maximum value, causing the mass spectrometer to perform an action based on the identification.

In some implementations, the separation device is a chromatography device, and wherein the introduction period is defined by a chromatographic elution peak width of the component.

In some implementations, the first maximum value is: (i) defined by a user, or (ii) defined based on a history of search results for candidate peptides not being identified before the corresponding elapsed search times reached a second maximum value, the second maximum value less than the first maximum value.

In some implementations, the first maximum value is less than or equal to 20 milliseconds (ms).

In some implementations, the candidate peptide is identified using amino acid sequences stored in the mass spectral database.

In some implementations, the candidate peptide is identified using empirically determined mass spectra stored in the mass spectral database.

In some implementations, the action to be performed based on the identification of the candidate peptide includes performing an additional stage of MSn analysis for one or more of the product ion species.

In some implementations, the action to be performed based on the identification of the candidate peptide includes refraining from performing an additional stage of MSn analysis for one or more of the product ion species.

In some implementations, the action to be performed based on the identification of the candidate peptide includes adjusting a fragmentation technique implemented by the fragmentation device used to fragment the peptide ions from a first fragmentation type to a second fragmentation type, the first fragmentation type and the second fragmentation type being different fragmentation types.

In some implementations, fragmentation is device configured to fragment the peptide ions to form second product ions, the mass analyzer is configured to analyze the second product ions to produce a second product ion spectrum, and the controller is further programmed with instructions for: executing a second search of the mass spectral database to attempt to identify a candidate peptide in the mass spectral database that matches the second product ion spectrum, while executing the search of the mass spectral database, monitoring a second elapsed search time of the second search and determining that the second elapsed search time exceeds the first maximum value, and upon identification of the second elapsed search time exceeding the first maximum value, terminating the second search.

Another innovative aspect of the subject matter described in this disclosure includes an apparatus including a mass analyzer configured to analyze product ions to produce a product ion spectrum; and a controller programmed with instructions for: identifying a candidate peptide using the product ion spectrum and a database including information related to mass spectrums of candidate peptides; while executing the search of the database, monitoring an elapsed search time, comparing the elapsed search time with a maximum search time value for performing the search of the database, and upon identification of the candidate peptide prior to the elapsed search time reaching the maximum search time value, causing the mass spectrometer to perform an action based on the identification.

DETAILED DESCRIPTION

Figure 1:
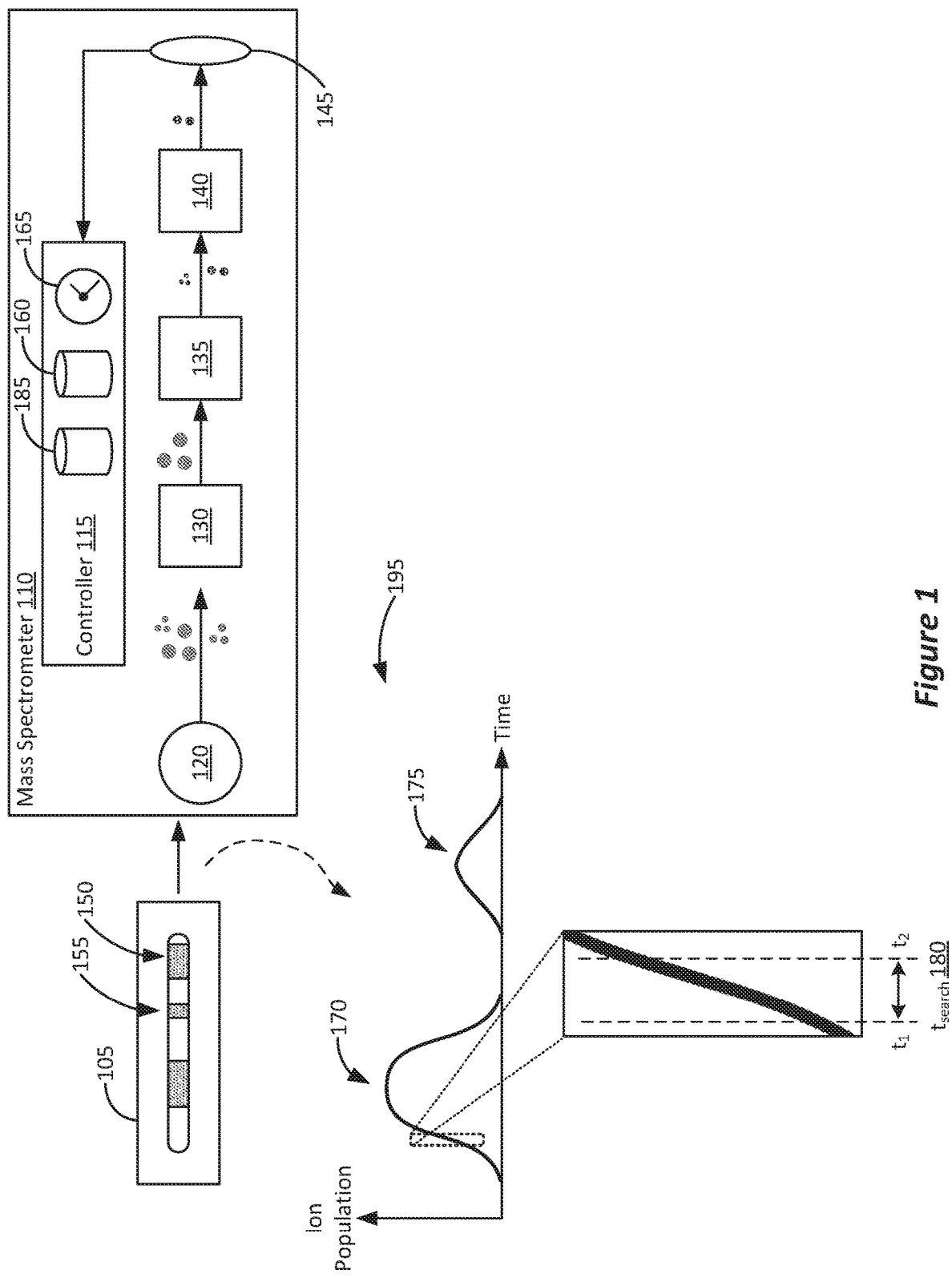
FIG. 1 illustrates an example of a mass spectrometer.

Some of the material described in this disclosure includes mass spectrometers and techniques for real-time searching (RTS). In one example, a mixture including peptides can be introduced into a chromatography system such that different peptides in the mixture are separated and introduced into a mass spectrometer for analysis at different times. The introduction period of a chromatographically separated peptide into the mass spectrometer (i.e., the time between when the peptide begins to elute from the chromatographic column and is delivered to the mass spectrometer inlet, and when elution is completed) is determined by the chromatographic peak width and defines the time available to perform mass spectrometry operations on the peptide.

In RTS for proteomics, an experimental mass spectrum generated by the mass spectrometer is used to search a mass spectral database. A mass spectral database includes an electronically-stored collection of information that includes either or both of (i) data, such as amino acid sequences for peptides and/or proteins, that may be employed to generate theoretical mass spectra based on predetermined rules (e.g., proteolysis cleavages, fragmentation predictions, etc.), or (ii) empirically derived spectra acquired previously for identified peptides (i.e., a spectral library), though other types of information related to peptides and/or proteins can also be stored. The theoretical or empirically-derived mass spectra contained in or derived from the mass spectral database includes a list of ion m/z's and optionally the corresponding measured or predicted intensities. If the experimental mass spectrum matches a candidate mass spectrum in the database, then the peptide that the experimental mass spectrum represents can be identified. Using data-dependent analysis (DDA) rules, if that peptide is of interest, then additional operations of the mass spectrometer can be performed on product ions of the peptide (e.g., MS3 operations can be performed). Alternatively, the DDA criterion can be set such that the performance or omission of a successive operation is dependent on whether the experimental spectra matches any candidate peptide in the database. This approach may be helpful to avoid performing further scans on non-peptidic substances in the sample matrix). These operations occur during the introduction time, or intake time, of the peptide.

As described later in this disclosure, the elapsed search time can be monitored and compared with a maximum search time. If the elapsed search time exceeds the maximum search time, then the RTS of the mass spectral database can be terminated. Instead of waiting for the search to complete, the mass spectrometer can perform the next operation (e.g., fragment a different precursor ion) rather than performing additional operations on the product ions (e.g., MS3 operations can be avoided). If the elapsed search time is completed prior to reaching the maximum search time, then the mass spectrometer can perform subsequent operations in dependence on the returned search results.

Since excessively long search times will reduce the number of data-dependent scans that can be performed, monitoring the elapsed search time in relation to the maximum search time can provide for more complete characterization of a sample by avoiding delays associated with prolonged search times and instead proceeding to another operation, which may yield important information regarding peptides or other components of the sample that are available within the mass spectrometer.

Figure 2:
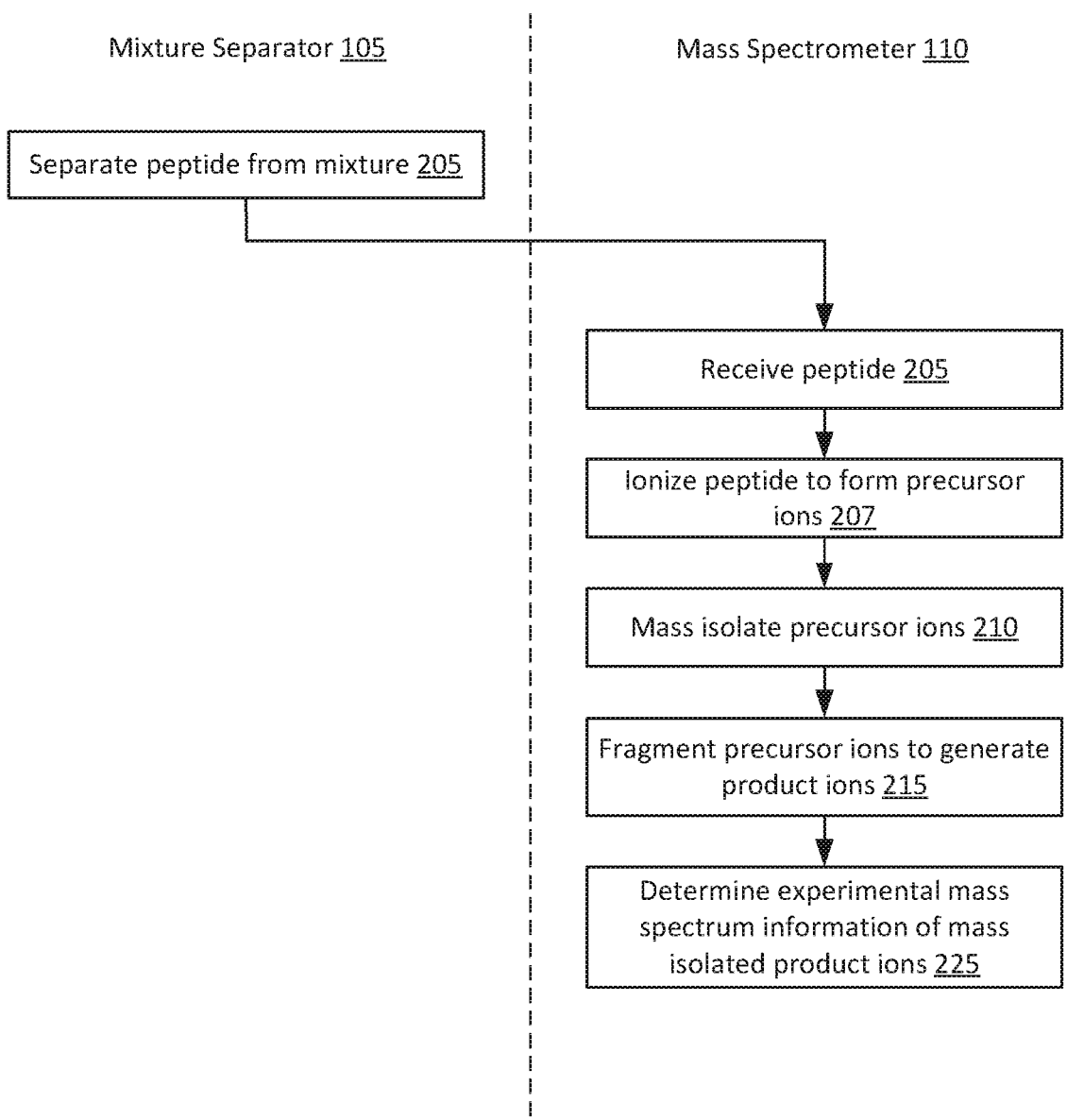
FIG. 2 illustrates an example of a block diagram for operating a mass spectrometer.

In more detail, FIG. 1 illustrates an example of a mass spectrometer. FIG. 2 illustrates an example of a block diagram for operating a mass spectrometer such as the example of FIG. 1 to acquire product ion mass spectra. In the block diagram of FIG. 2, a peptide is separated from other peptides (and other components) in a mixture (205). For example, in FIG. 1, mixture separator 105 can be a liquid chromatography (LC), gas chromatography (GC), capillary electrophoresis (CE), or other type of system used to separate components of a mixture. In the example of proteins subject to digestion, the separate components of the mixture are peptides (e.g., fragments of the protein).

In FIG. 1, mixture separator 105 is depicted as separating a peptide mixture into several components including peptides 150 and 155. Peptides 150 and 155 are separated in space, or position, along a flow path (for example, within a chromatographic column) such that peptides 150 and 155 are introduced into mass spectrometer 110 at different times. This is depicted with chromatogram 195 showing peaks 170 and 175 representing peptides 150 and 155, respectively. Different peptides can have a different abundance within the mixture and, therefore, each of the peaks appears differently.

Returning to the block diagram of FIG. 2, the peptide can then be provided to the mass spectrometer (205) and the peptide can be ionized to form precursor ions (207). For example, in FIG. 1, when peptide 150 is introduced into mass spectrometer 110, it is first provided to ion source 120. Ion source 120 can ionize a material under analysis by removing or adding charge-carrying entities (e.g., hydrogen nuclei or electrons) to or from the material to provide the material with a positive or negative charge. This results in precursor ions forming from the ionization of peptide 150. Ion source 120 will typically be of the electrospray ionization (ESI) type, but may instead utilize any other suitable ionization technique, including atmospheric-pressure chemical ionization (APCI) or atmospheric pressure photoionization (APPI).

Next, in FIG. 2, the precursor ions are mass isolated (210). For example, in FIG. 1, the precursor ions of the peptide formed by ion source 120 are transported via appropriate ion optics to mass selector 130. Mass selector 130 may take the form, in one example, of a quadrupole mass filter in which the amplitudes of the radio-frequency (RF) and resolving direct current (DC) voltages are adjusted such that only ions within a narrow range of m/z values are transmitted. Alternatively, mass selector 130 may be any suitable device capable of isolating ions within a m/z window of interest, such as an analytical ion trap or time-of-flight (TOF) mass analyzer. As depicted in FIG. 1, some of the precursor ions of the peptide are thus mass selected and passed onwards to fragmentation cell 135. In other words, some of the precursor ion species are mass isolated.

In FIG. 2, the precursor ions are fragmented to generate product ions (215). For example, in FIG. 1, fragmentation cell 135 receive the precursor ions from mass analyzer 130 and fragments, or breaks up, the precursor ions into smaller product ions. Fragmentation is often performed on larger molecules, such as peptides, to allow for more detailed understanding of the structural composition of the peptide. Fragmentation cell 135 can be implemented using many different types of disassociation techniques including collision-induced disassociation (CID), surface-induced dissociation (SID), electron-capture dissociation (ECD), electron-transfer dissociation (ETD), negative electron-transfer dissociation (NETD), electron-detachment dissociation (EDD), photodissociation, higher-energy C-trap dissociation (HCD), etc.

Next, in FIG. 2, the product ions are subjected to mass analysis to yield an experimental mass spectrum (225). For example, in FIG. 1, the product ions formed by fragmentation cell 135 are provided to a mass analyzer 140, mass separated, and then provided to detector 145. Mass analyzer 140 can be any suitable device for separating ions according to their mass-to-charge ratios, including (without limitation) an orbital electrostatic trap, analytical quadrupole ion trap, Fourier Transform-Ion Cyclotron Resonance (FT-ICR) analyzer, TOF mass analyzer, or a quadrupole mass filter.

Detector 145 can detect induced charge or current produced when the product ions provided by mass analyzer 140 pass by or hit a surface of detector 145. Thus, detector 145 can generate signals representative of the m/z of the product ions. These signals can be provided to controller 115, which can then generate a mass spectrum using the detected signals.

In FIG. 1, mass spectrometer 110 is a tandem mass spectrometer configured to implement a single stage of mass isolation and fragmentation, as indicated with the arrangement of fragmentation cell 135 between mass selector 130 and mass analyzer 140. This is often referred to as MS/MS or MS2 mass spectrometry. In certain implementations, it may be desirable to perform further stages of isolation and fragmentation of generations of product ions (e.g., MS3, MS4, MS5, etc. wherein n is a positive integer). In such cases, the components of mass spectrometer 110 may be configured to effect the additional isolation/fragmentation operations. For example mass analyzer 140 may be an analytical quadrupole ion trap mass analyzer that, in addition to performing the mass separation function for acquiring mass spectra, is also capable of executing steps of mass isolation and fragmentation.

For example, in FIG. 1, controller 115 can be a programmed controller circuit that can analyze the experimental mass spectrum generated using the signals provided by detector 145. Database 160 can be a database storing data related to theoretical mass spectrums for many different peptides (e.g., based on amino acid sequences, empirically determined mass spectra (e.g. based on prior observations or experiences), or other information as discussed later herein). As discussed in further detail below, controller 115 may be programmed to search the database to determine which, if any, of the candidate peptides contained in the database have (theoretical or empirically determined) mass spectra that match the experimentally acquired mass spectrum, thereby establishing, to a reasonable degree of confidence, that the sample component that produced the experimental mass spectrum is the matching candidate peptide in the database.

Using DDA rules database 185, controller 115 can further determine whether the peptide is of interest for further analysis and, if so, perform MS3 on the product ions to generate additional information for the peptide. If the peptide is not of interest or if no matching peptides are returned, then an additional MS3 operation can be refrained from being performed. Rather, different precursor ions can be selected or fragmented differently to form other product ions for analysis.

However, because peptide 150 is only provided to mass spectrometer 110 for a short time (as depicted in chromatograph 195 with peak 170), the searching of database 160 for a matching peptide must be performed relatively quickly while peptide 150 is still available. For example, as depicted in FIG. 1, $t_{search}$ 180 (indicating the elapsed search time for conducting the search of database 160 for a possible match) is performed while the abundance of peptide 150 is available to mass spectrometer 110. Thus, a smaller $t_{search}$ 180 (i.e., faster elapsed search time) can allow for more MS scans of peptide 150, resulting in a higher throughput for mass spectrometer 110, more data collection, and less waste of peptide 150.

In FIG. 1, controller 115 can implement timer 165, which can be used to measure or determine the elapsed search time $t_{search}$ 180 by incrementing a counter when the experimental mass spectrum is received or when the search begins. If the elapsed search time exceeds a maximum value, then the search of database 160 for a match can be terminated. This can result in skipping MS3 for the product ions, and performing a new MS2 scan for different precursor ions of peptide 150. If $t_{search}$ 180 is less than the maximum value, then the search is continued until a matching peptide is returned or it is determined that no matching peptide is present. When a matching peptide is returned prior to reaching the maximum value, mass spectrometer 110 can be instructed to perform an action based on the identification of the candidate peptide, for example, perform MS3. After MS3, a new MS2 scan for different precursor ions can be performed.

Figure 3:
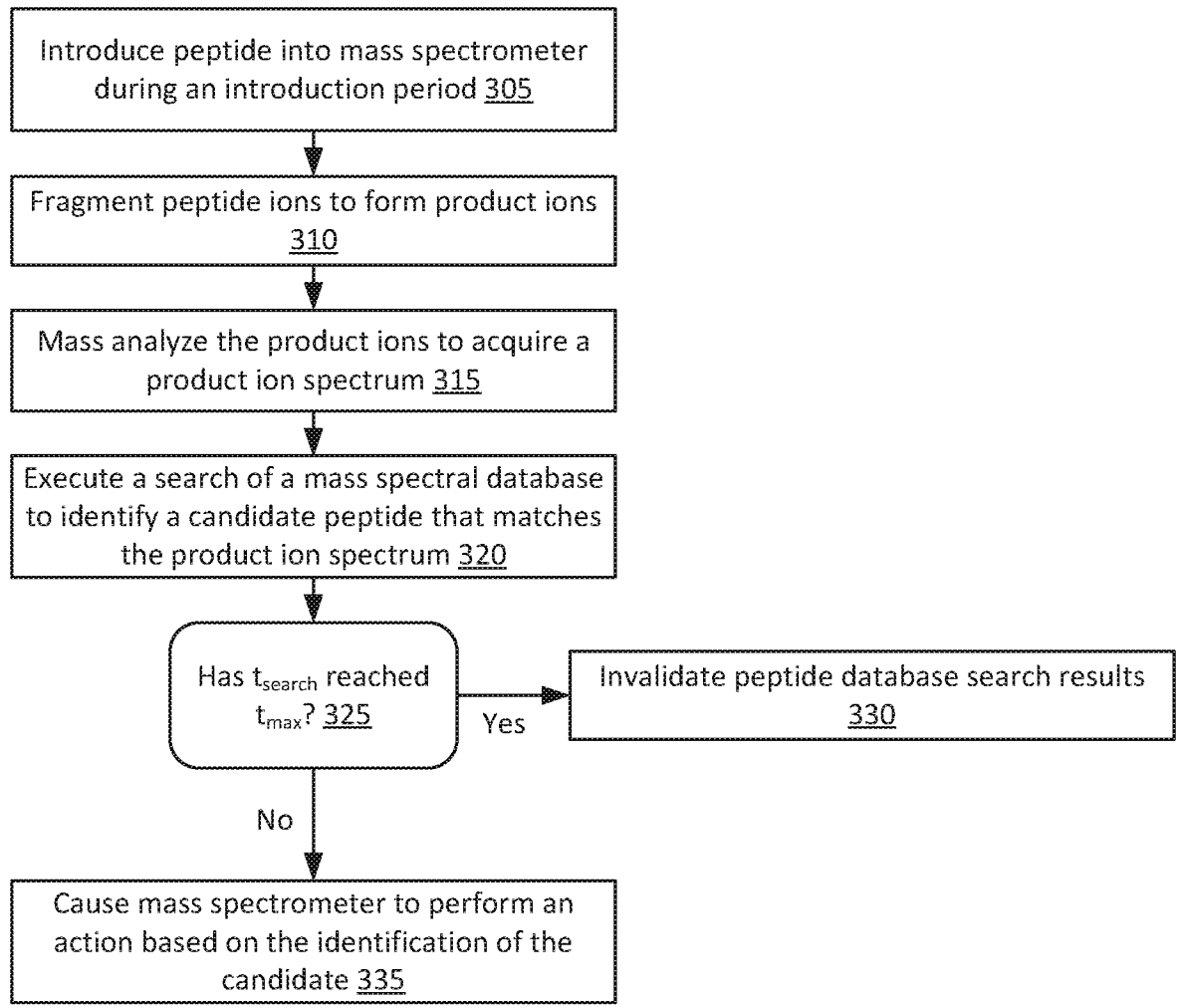
FIG. 3 illustrates an example of a block diagram performing a real-time search (RTS) for a mass spectrometer.
Figure 4:
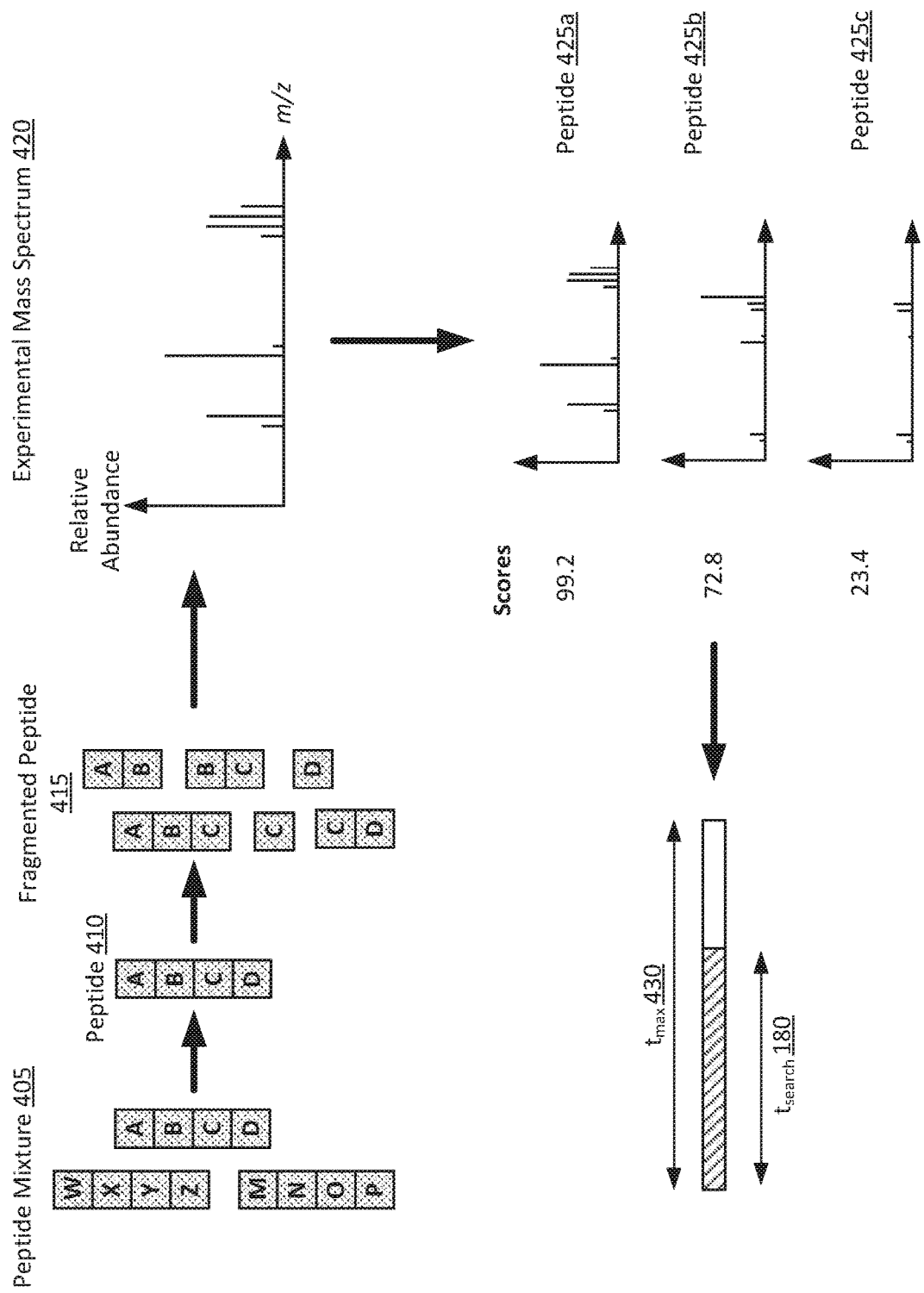
FIG. 4 illustrates an example of performing a RTS for a mass spectrometer.

More detail regarding the RTS techniques will now be described in relation to FIGS. 3 and 4. FIG. 3 illustrates an example of a block diagram performing a RTS for a mass spectrometer. FIG. 4 illustrates an example of performing a RTS for a mass spectrometer. As discussed with reference to FIG. 1, a mixture with peptides can be separated such that the different components are provided to mass spectrometer 110 at different times (i.e., temporally separated). In FIG. 4, the mixture to be separated is depicted as peptide mixture 405, and peptide 410 is a peptide that is isolated from other peptides of the mixture and provided to mass spectrometer 110. Thus, in FIG. 3, the peptide can be introduced into the mass spectrometer during an introduction period (305) and ionized to form peptide ions. The peptide ions can undergo fragmentation to form product ions (310). In FIG. 4, this is depicted as fragmented peptide 415.

Next, in FIG. 3, the product ions can be mass analyzed to acquire a product ion spectrum (315). In FIG. 4, this is depicted as experimental mass spectrum 420, which provides a plot of the relative abundance of the product ions vs. the m/z of the product ions.

Returning to FIG. 3, a search of a mass spectral database can then be executed to identify a candidate peptide that matches the product ion spectrum (320). That is, the experimental mass spectrum generated by mass spectrometer 110 for the product ions is used to search database 160 in FIG. 1 to identify a match with a theoretical or empirical mass spectrum stored in the mass spectral database. Because each of the theoretical or empirical mass spectrum can be tied with a peptide, identifying a match between the experimental mass spectrum and the theoretical or empirical mass spectrum provides an identification of a peptide as a candidate for the peptide introduced into mass spectrometer 110.

The identification of the candidate peptide can include a variety of algorithms. In the example of FIG. 4, a score representing a confidence, or likelihood of a match, is generated for some or all of the mass spectra stored in database 160. The highest score can be used to identify the peptide candidate as the match, which is depicted as peptide 425a in FIG. 4, while peptides 425b and 425c have lower scores and, therefore, are not identified as matches. However, other algorithms can include additional metrics, for example, requiring a score to be within a threshold value range to be identified as a match.

As previously discussed, database 160 can store different types of information for the theoretical or empirical mass spectra. For example, the information can include amino acid sequences or empirically determined or derived mass spectra. Additionally, the identification of the peptide candidate can include matching the m/z positions on the x-axis and relative abundance on the y-axis of experimental mass spectrum 420 with the stored information. However, other applications might use less or more information. For example, for faster searching, only the m/z positions (or a peak list) on the x-axis of experimental mass spectrum 420 are used to identify a candidate peptide. Some examples of algorithms that can be used for protein and peptide identification include SEQUEST, Mascot, MOWSE, COMET, etc.

Returning to FIG. 3, while the search is being executed, the elapsed search time can be monitored to determine if it has reached a maximum search time (325) and if the elapsed search time has reached the maximum search time then the search can be terminated (330). For example, at the termination of the search, the mass spectrometer can resume a new MS2 scan for different precursor ions. However, if the search for the candidate peptide has completed (returning either a result that the experimental mass spectrum matches that of a candidate peptide, or alternatively that no matched candidate peptides were found) prior to the elapsed search time reaching the maximum value, then the mass spectrometer can be caused to perform an action based on the search result, e.g., the identification of the matching candidate peptide (335). For example, in FIG. 4, if $t_{search}$ 180 (i.e., the elapsed search time) is less than $t_{max}$ 430 (i.e., the maximum search time), then peptide 425a can be identified as the candidate peptide of experimental mass spectrum 420 and, therefore, identify peptide 410.

In one example, the maximum search time might be 20 milliseconds (ms) and an average elapsed search time might be 10 ms. Thus, the 20 ms maximum search time can allow for ample room to identify a candidate peptide for most searches. Additionally, because the total introduction period can vary in the tens of seconds to several minutes, the maximum search time ensures that many searches can be performed.

Figure 5:
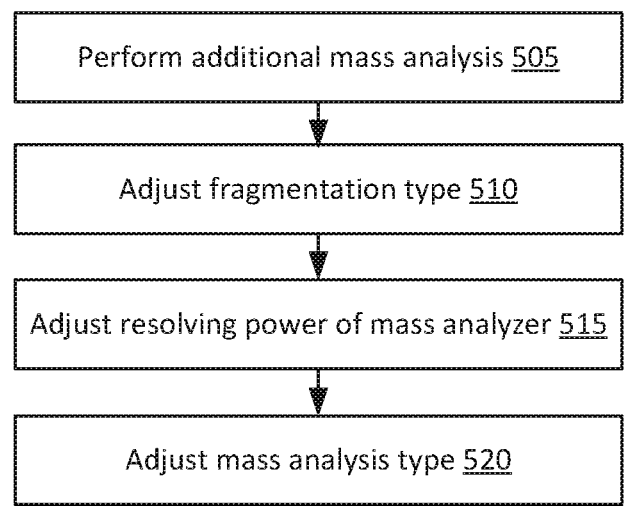
FIG. 5 illustrates an example of a block diagram for adjusting operational parameters of a mass spectrometer.
Figure 6:
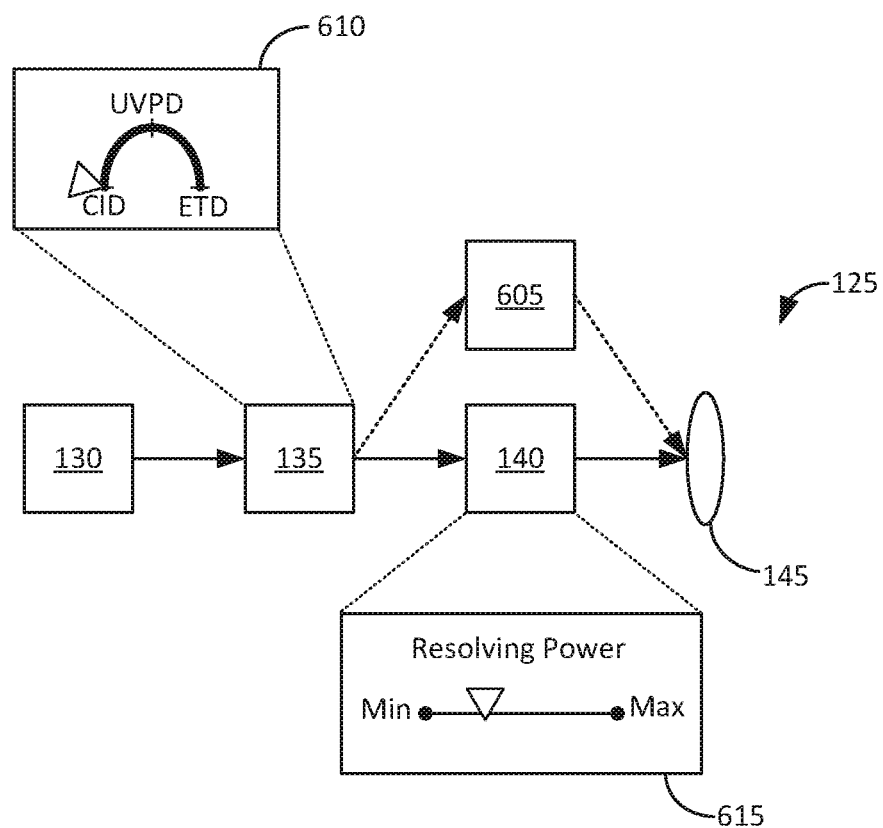
FIG. 6 illustrates an example of adjusting operational parameters of a mass spectrometer.

The actions that can be performed upon the identification of the candidate peptide include adjusting different operational parameters of the mass spectrometer, as will be described with reference to FIGS. 5 and 6. FIG. 5 illustrates an example of a block diagram for adjusting operational parameters of a mass spectrometer. FIG. 6 illustrates an example of adjusting operational parameters of a mass spectrometer. In the block diagram of FIG. 5, additional mass analysis can be performed (505). For example, mass spectrometer 110 in FIG. 1 can be configured by controller 115 to perform MS3 on the product ions. Performing MS3 on the product ions includes performing an additional stage of mass isolation and fragmentation to generate another experimental mass spectrum, this time for the fragments of the product ions. The additional MS3 scan can provide additional information regarding the sample components.

Moreover, an additional MS3 (or other MSn) operation can be refrained from being performed based upon the identification. For example, if the candidate peptide that is identified is one that is not of interest for the experimentation (e.g., as indicated in DDA rules database 185) or alternatively that no matching peptides have been found, then MSn can be refrained from being performed.

According to a specific implementation of the methods disclosed herein, a maximum search time-limited RTS routine may be utilized in connection with the reporter ion-based multiplexed peptide quantification technique described by McAlister et al., "MultiNotch MS3 Enables Accurate, Sensitive and Multiplexed Detection of Differential Expression Across Cancer Cell Line Proteomes", Analytical Chemistry, Vol. 86, pp. 7150-7158 (2014), the disclosure of which is incorporated herein by reference. In accordance with this technique, chemically tagged peptide-containing samples are analyzed to identify differential expression of peptides between or among samples, with relative quantitation being achieved by measurement of reporter ions signal (each sample being chemically tagged with a reagent having a reporter ion of distinct mass-to-charge ratio). In order to reduce or avoid the effect of interfering, co-eluting species on the calculation of relative abundance, an MS3 approach is utilized, wherein the precursor ions produced by ionization of the sample are subjected to two successive stages of isolation and fragmentation. However, it may be inefficient to perform MS3 if the MS2 product ion spectra reveal that no matching peptides of interest are present. To address this problem, the RTS routine may be employed to assess whether or not the MS2 spectrum matches a candidate peptide of interest contained in the database; if so, the method proceeds to acquire a MS3 spectrum, and if not, the method proceeds to select a different precursor ion for acquisition of a product ion spectrum. The time constraint imposed by the maximum search time limit ensures that the use of the RTS routine does not excessively reduce the number of data points that may be acquired across a chromatographic peak.

Returning to FIG. 5, other operational parameters that can be adjusted include a fragmentation type (510), resolving power of a mass analyzer (515), or adjusting a mass analysis type (520). In FIG. 6, adjusting the fragmentation type is depicted in a simplified example as fragmentation type 610. Fragmentation type 610 depicts the option to switch among the different fragmentation techniques to be used to fragment precursor ions, though all the fragmentation techniques described herein can be switched among and other fragmentation cells might be used for some of the techniques. That is, the mass spectrometer can include multiple fragmentation cells to implement different types of fragmentation techniques. Using a different fragmentation type can allow for additional data collection to complement the previously-acquired experimental mass spectrum.

Regarding adjusting the resolving power of a mass analyzer, this is depicted in a simplified example as resolving power 615 in FIG. 6. Increasing the resolving power of mass analyzer 140 can improve the ability of mass spectrometer 110 to distinguish between two peaks in experimental mass spectrum 420 that are of slightly different m/z. That is, two m/z values that are of slightly different m/z can be identified with separate and distinct peaks of a mass spectrum. For example, by collecting a longer transient (e.g., the time used for collection and detection of the product ions) on an Orbitrap mass analyzer, the resolving power of the mass analyzer is increased than when collecting a shorter transient.

Regarding adjusting the mass analysis type, in some implementations, other mass analyzers can be used. For example, a first experimental mass spectrum can be generated using a mass analyzer with a lower resolution or lower mass accuracy. If the first experimental mass spectrum yields a candidate peptide during the search (and within the maximum search time for the elapsed search time), then analysis can be performed a second time using another mass analyzer with different performance characteristics, for example, with a higher resolution or a higher mass accuracy than the first mass analyzer. In some implementations, the maximum search time using the results of the first mass analyzer can be shorter than the maximum search time using the results of the second mass analyzer due to the increase in data collected. In FIG. 6, this is depicted as using mass analyzer 605 rather than mass analyzer 140. A second experimental mass spectrum can then be generated. Because the second mass analyzer had better performance characteristics, a higher resolution second experimental mass spectrum is generated that can provide more information or features to be used to provide a more confident identification of the candidate peptide.

As previously discussed, in RTS, the searching is performed while the peptide is present and available for experimentation within the mass spectrometer. For example, after the ionization of the peptide by the ion source, the peptide ions are available for mass selection and fragmentation and, therefore, the experimental mass spectrum can be generated and an MS3 scan can be performed by matching the experimental mass spectrum with the mass spectrum of a peptide candidate. Thus, RTS can be performed relatively quickly such that many experimental mass spectra are determined and many decisions are made regarding whether to perform MS3, and to perform MS3, while the peptide is ionized.

Figure 7:
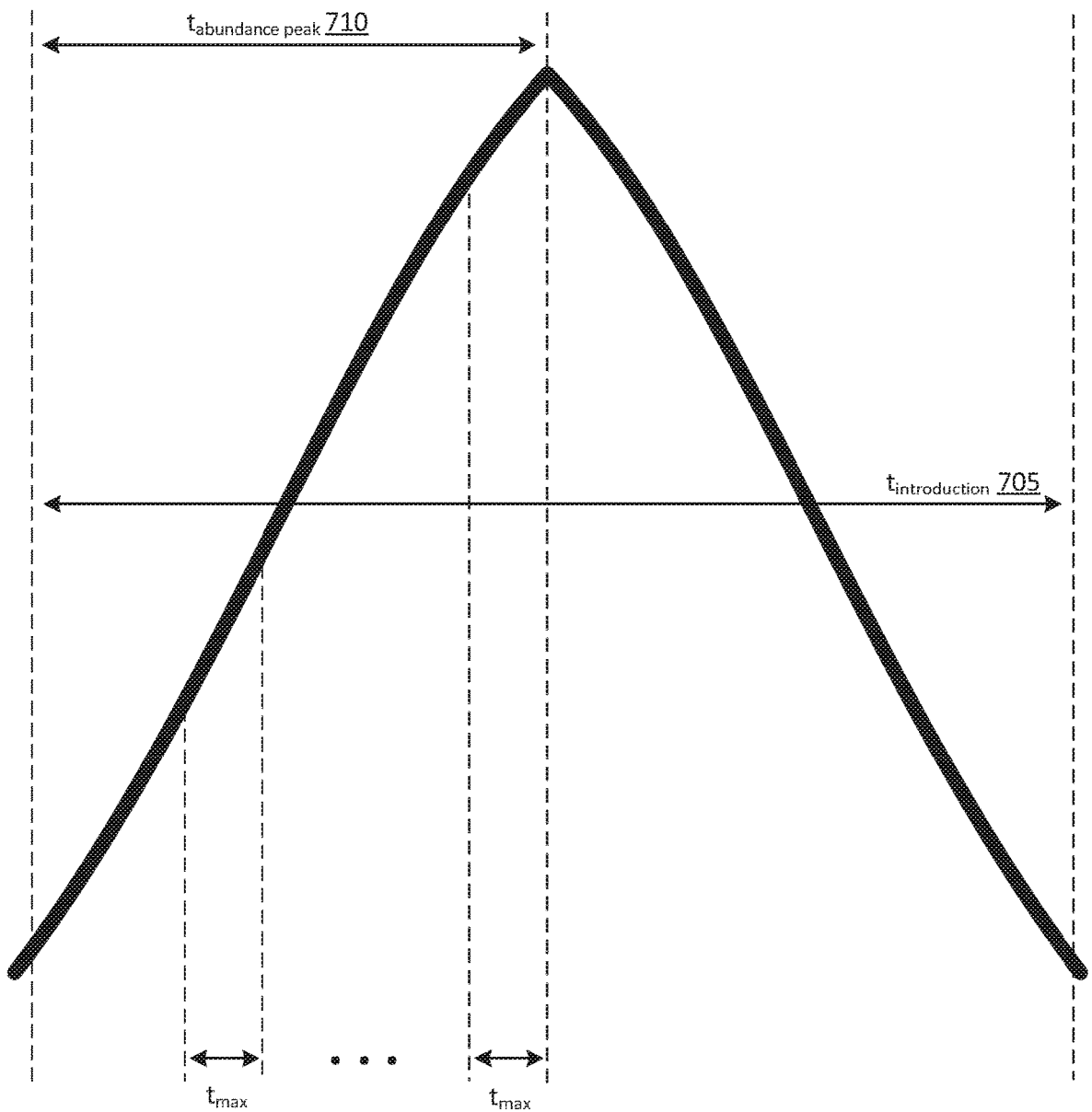
FIG. 7 illustrates an example of an introduction of an analyte to a mass spectrometer.

FIG. 7 illustrates an example of an introduction of an analyte to a mass spectrometer. In FIG. 7, the x-axis represents time and the y-axis represents abundance of an analyte under experimentation, for example, a peptide as previously discussed. In FIG. 7, $t_{introduction}$ 705 represents the introduction time, or intake time, that the peptide ions are available. The abundance of the peptide increases from zero to a peak at $t_{abundance\,peak}$ 710, and then declines from the peak to zero at the end of $t_{introduction}$ 705. This is similar to the chromatographically separated peptide of the sample if a chromatographic technique for mixture separator 105 was used. Thus, $t_{introduction}$ 705 can be defined by a chromatographic elution peak width of the component that is separated (e.g., peptide 150 in FIG. 1 or peptide 410 in FIG. 4). To improve the quality of the experimental mass spectrum, generation of the experimental mass spectra can be performed while the abundance of the peptide ions occurs within a threshold level, for example, centered around the peak, though in some implementations the various operations to generate the experimental mass spectra can be performed only on the rising slope. Each of the elapsed search times should be within $t_{max}$, otherwise the search can be terminated, as previously discussed.

The maximum search time, or $t_{max}$, can be indicated by an operator or user (e.g., via a graphical user interface (GUI) of a software system implemented using controller 115) or automatically set to a default value. However, the maximum search time can also be dynamically adjusted by controller 115 during or after the introduction time, $t_{introduction}$. Moreover, the content of database 160 can also be modified during or after the introduction time.

Figure 8:
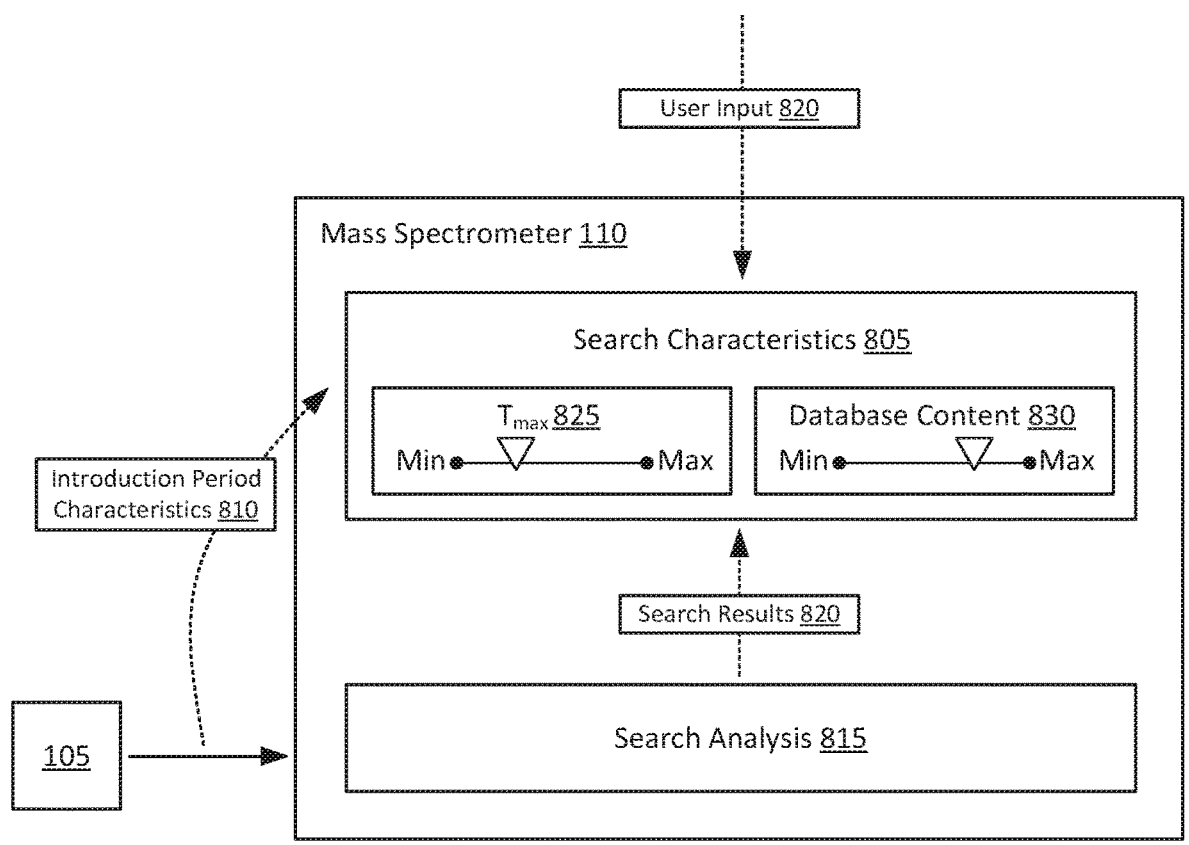
FIG. 8 illustrates an example of adjusting RTS characteristics.
Figure 9:
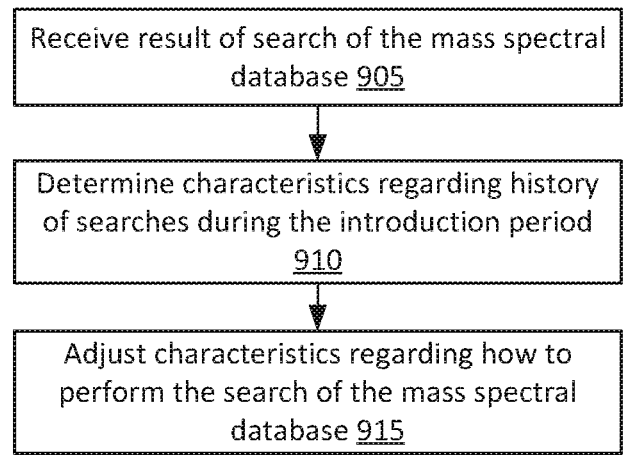
FIGS. 9 and 10 illustrate examples of block diagrams for adjusting RTS characteristics.
Figure 10:
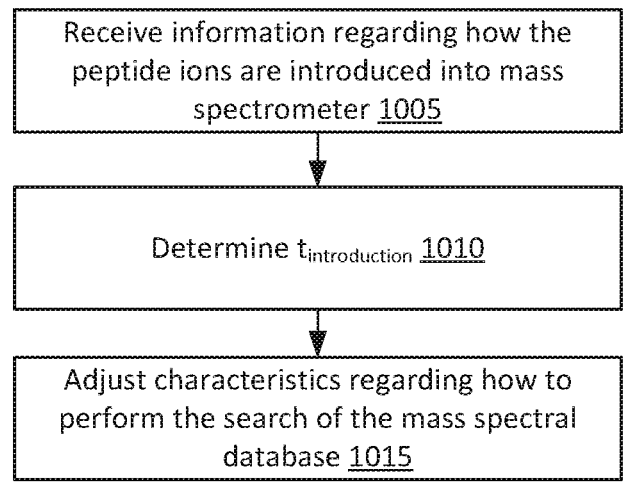

In more detail, FIG. 8 illustrates an example of adjusting RTS characteristics. FIGS. 9 and 10 illustrate examples of block diagrams for adjusting RTS characteristics. In FIG. 8, controller 115 implements logic or functionality including search characteristics 805 which governs how the search is to be performed, as well as search analysis 815 which performs the RTS for the candidate peptide using the experimental mass spectrum and the database. In the case where the maximum search time is dictated by a user, user input 820 is received and $t_{max}$ 825 is established to match user input 820.

However, in some implementations, the maximum search time, $t_{max}$ 825, can be adjusted during the introduction time by identifying a history of search results or how the peptide ions are being introduced. This can allow for changes from user input 820 and ensure that more data is collected if user input 820 provides a maximum search time that is too short and resulting in many terminated searches.

For example, in FIG. 9, the result of a search of the mass spectral database can be received (905). In FIG. 8, this is depicted as search results 820 being provided by search analysis 815 to search characteristics 805. Search results 820 can indicate whether a candidate peptide was identified within the maximum search time, or if the search was terminated due to the elapsed search time exceeding the maximum search time. Search results 820 can then be stored (e.g., in a memory device such as a database). Returning to the block diagram of FIG. 9, characteristics regarding the history of searches during the introduction period can then be determined (910). For example, if a certain number of failed searches (e.g., terminated searches due to the elapsed search time exceeding the maximum search time) have occurred in a row, or if the number of failed searches has reached a certain number during the introduction period, then this can be identified. The controller can then adjust characteristics regarding how to perform the search of the mass spectral database (915). For example, in FIG. 8, the maximum search time, $t_{max}$ 825, can be increased such that more time can be spent searching for the candidate peptide (i.e., the elapsed search time can go on longer before terminating the search).

Additionally, database content 830 can be modified to allow for less of the database content to be searched. By searching less content, the search for the candidate peptide might be faster at the cost of having some experimental mass spectra be indicated as lacking a candidate peptide due to a possible match not being included in the search. In one example, the database can include additional data regarding the candidate peptides including annotations regarding the protein that the candidate peptide is derived from or the candidate peptide itself. For example, the type of animal (e.g., mouse) or the organ system (e.g., liver) can be annotated for each of the candidate peptides. Database content 830 can then be reduced by only searching for peptide candidates that fit within a constraint on the annotations, for example, only peptides that occur in proteins from mouse livers might be searched.

Additionally, $t_{max}$ 825 or database content 830 can be modified based on how the peptide ions are provided during the introduction period. For example, a sensor disposed within the mixture separation system, before the ion source, or after the ion source, can be used to determine how the peptide or peptide ions are introduced to the mass analyzer. This is depicted in FIG. 8 as introduction period characteristics 810 being provided to search characteristic 805. Introduction period characteristics 810 can include the rate of change in the abundance, identify whether the abundance is increasing or decreasing or has reached the peak, the slope, the current abundance, or other determinations calculated in accordance with operating conditions and parameters; for example, $t_{max}$ 825 may be adjusted based on the chromatographic peak width, the spectral scan rate, the numbers of precursor ion species to be analyzed, etc.

Using this information, the introduction period can be determined or estimated and used to determine the maximum search time to ensure a minimum number of MS scans to be performed. However, in other implementations, other time frames can be determined and used to set the maximum search time. For example, $t_{abundance\,peak}$ 710 in FIG. 7 can be determined or estimated.

Thus, in FIG. 10, information regarding how the peptide ions are introduced into the mass spectrometer are received (1005). Based on this information, the introduction period $t_{introduction}$ can be estimated (1010) and used to adjust the characteristics regarding how to perform the search of the mass spectral database (1015). For example, based on the estimated introduction period, the maximum search time can be estimated. The maximum search time can be set to ensure a certain number of searches during the introduction period. Additionally, database content 830 can also be adjusted as similarly discussed with respect to FIG. 9.

Many of the examples describe implementations with liquid chromatography-tandem mass spectrometry (LC-MS/MS) for the identification of peptides. However, other types of mixture separation can be used including gas chromatography (GC) or capillary electrophoresis (CE).

The examples describe techniques for the RTS for a candidate peptide, however, other biomolecules can be identified and the mass spectrometer can perform a specific action upon the identification. For example, in addition to proteins and their peptides, other types of biomolecules that can be used with the techniques include lipids, nucleic acids, metabolites, oligosaccharides, polysaccharides, and the like. Moreover, other large molecules other than biomolecules can be identified, in addition to small molecules. Thus, the experimental mass spectrum can be generated for many different types of molecules, the database can store information related to possible candidates, and the RTS can be performed to identify a candidate.

The tandem mass spectrometers described in the examples can be triple quadrupole mass spectrometers (QqQ), quadrupole time-of-flight mass spectrometers (QqTOF), or other types of mass spectrometers. Additionally, while the examples describe tandem mass spectrometry in space, tandem mass spectrometry in time can also be used with the techniques described herein. In a tandem mass spectrometer in time, a single mass analyzer can be used. Moreover, more than two mass analyzers can be disposed within the mass analyzer, as also discussed with the example of FIG. 6.

The databases described in the examples are stored locally with the controller system of the mass spectrometer. However, cloud-based implementations can also be used in which the databases are stored on a remote server that is accessible by the controller. Additionally, hybrid approaches can be implemented with the RTS techniques. For example, a smaller database stored in the system of the mass spectrometer can be searched in parallel with a larger database stored in a remote server. A hybrid approach can allow for a smaller dataset that includes higher likelihood candidate peptides to be identified relatively quickly. If the peptide under analysis is not identified with the local database, the remote database can search a larger dataset to attempt to identify a candidate peptide.

Figure 11:
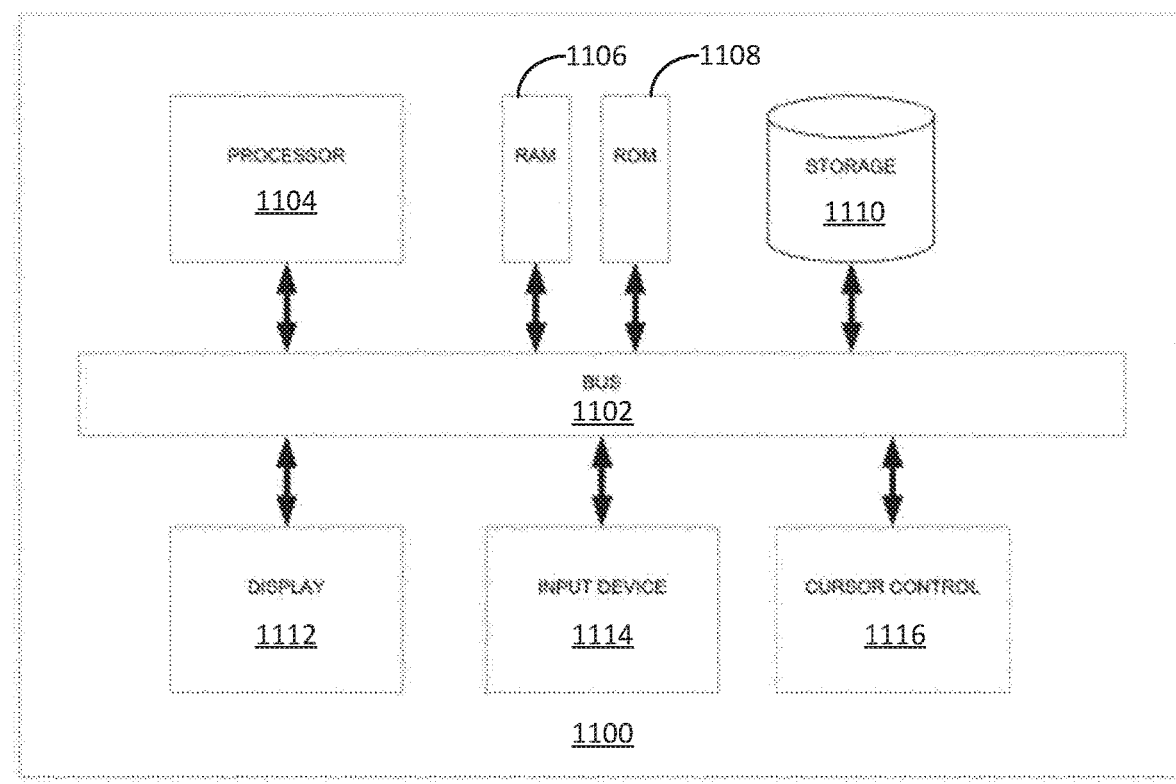
FIG. 11 illustrates an example of an electronic device which may be used to implement some of the examples.

FIG. 11 illustrates an example of an electronic device which may be used to implement some of the implementations. The electronic device of FIG. 11 can store or use a computer program product including one or more non-transitory computer-readable media having computer programs instructed stored therein, the computer program instructions being configured such that, when executed by one or more computing devices, the computer program instructions cause the one or more computing devices to: cause introduction of peptide ions generated from the biological sample into a mass spectrometer during an introduction period; fragment the peptide ions to form product ions; mass analyze the product ions to acquire a product ion spectrum; and during the introduction period, execute a search of a mass spectral database to attempt to identify a candidate peptide in the mass spectral database that matches the product ion spectrum, the mass spectral database containing product mass spectral information for candidate peptides, while executing the search of the mass spectral database, monitoring an elapsed search time, and upon identification of the candidate peptide that matches the product ion spectrum prior to the elapsed search time reaching a first maximum value, causing the mass spectrometer to perform an action based on the identification.

In FIG. 11, computer system 1100 can implement any of the methods or techniques described herein. For example, computer system 1100 can implement controller 115 in FIG. 1. Thus, the operation of components of the associated mass spectrometer may be adjusted in accordance with calculations or determinations made by computer system 1100. In various embodiments, computer system 1100 can include a bus 1102 or other communication mechanism for communicating information, and a processor 1104 coupled with bus 1102 for processing information. In various embodiments, computer system 1100 can also include a memory 1106, which can be a random access memory (RAM) or other dynamic storage device, coupled to bus 1102, and instructions to be executed by processor 1104. Memory 1106 also can be used for storing temporary variables or other intermediate information during execution of instructions to be executed by processor 1104. In various embodiments, computer system 1100 can further include a read only memory (ROM) 1108 or other static storage device coupled to bus 1102 for storing static information and instructions for processor 1104. A storage device 1110, such as a magnetic disk or optical disk, can be provided and coupled to bus 1102 for storing information and instructions.

In various embodiments, computer system 1100 can be coupled via bus 1102 to a display 1112, such as a cathode ray tube (CRT) or liquid crystal display (LCD), for displaying information to a computer user. An input device 1114, including alphanumeric and other keys, can be coupled to bus 1102 for communicating information and command selections to processor 1104. Another type of user input device is a cursor control 1116, such as a mouse, a trackball or cursor direction keys for communicating direction information and command selections to processor 1104 and for controlling cursor movement on display 1112. This input device typically has two degrees of freedom in two axes, a first axis (i.e., x) and a second axis (i.e., y), that allows the device to specify positions in a plane.

A computer system 1100 can perform the techniques described herein. Consistent with certain implementations, results can be provided by computer system 1100 in response to processor 1104 executing one or more sequences of one or more instructions contained in memory 1106. Such instructions can be read into memory 1106 from another computer-readable medium, such as storage device 1110. Execution of the sequences of instructions contained in memory 1106 can cause processor 1104 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations described herein are not limited to any specific combination of hardware circuitry and software.

The term "computer-readable medium" as used herein refers to any media that participates in providing instructions to processor 1104 for execution. Such a medium can take many forms, including but not limited to, non-volatile media, volatile media, and transmission media. Examples of non-volatile media can include, but are not limited to, optical or magnetic disks, such as storage device 1110. Examples of volatile media can include, but are not limited to, dynamic memory, such as memory 1106. Examples of transmission media can include, but are not limited to, coaxial cables, copper wire, and fiber optics, including the wires that comprise bus 1102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the techniques are described in conjunction with various implementations or embodiments, it is not intended that the techniques be limited to such embodiments. On the contrary, the techniques encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

I claim:

1. A method of operating a mass spectrometer to analyze a biological sample, comprising:
   introducing peptide ions generated from the biological sample into the mass spectrometer during an introduction period;
   fragmenting the peptide ions to form product ions;
   mass analyzing the product ions to acquire a product ion spectrum; and
   during the introduction period, using a programmed controller to perform:
      executing a search of a mass spectral database to attempt to identify a candidate peptide in the mass spectral database that matches the product ion spectrum, the mass spectral database containing product mass spectral information for candidate peptides,
      while executing the search of the mass spectral database, monitoring an elapsed search time,
      upon identification of the candidate peptide that matches the product ion spectrum prior to the elapsed search time reaching a first maximum value that is shorter than the introduction period, causing the mass spectrometer to perform an action based on the identification, and
      terminating the search when the elapsed search time reaches the first maximum value.

2. The method of claim 1, wherein introducing peptide ions includes ionizing a chromatographically separated component of the biological sample, the introduction period being defined by a chromatographic elution peak width of the component.

3. The method of claim 1, wherein the first maximum value is defined by a user.

4. The method of claim 1, wherein the first maximum value is defined based on a history of search results for candidate peptides not being identified before corresponding elapsed search times reached a second maximum value, the second maximum value less than the first maximum value.

5. The method of claim 1, wherein fragmenting the peptide ions includes mass isolating at least one ion species prior to fragmentation.

6. The method of claim 1, wherein the first maximum value is less than or equal to 20 milliseconds (ms).

7. The method of claim 1, wherein the candidate peptide is identified using amino acid sequences stored in the mass spectral database.

8. The method of claim 1, wherein the candidate peptide is identified using empirically determined mass spectra stored in the mass spectral database.

9. The method of claim 1, wherein the action to be performed based on the identification of the candidate peptide includes performing an additional stage of MSn analysis for one or more of the product ion species.

10. The method of claim 1, wherein the action to be performed based on the identification of the candidate peptide includes refraining from performing an additional stage of MSn analysis for one or more of the product ion species.

11. The method of claim 1, wherein the action to be performed based on the identification of the candidate peptide includes adjusting a fragmentation technique implemented by a fragmentation cell used to fragment the peptide ions from a first fragmentation type to a second fragmentation type, the first fragmentation type and the second fragmentation type being different fragmentation types.

12. The method of claim 1, further comprising:
fragmenting the peptide ions to form second product ions;
mass analyzing the second product ions to acquire a second product ion spectrum; and
during the introduction period, using the programmed controller to perform:
    executing a second search of the mass spectral database to attempt to identify a candidate peptide in the mass spectral database that matches the second product ion spectrum,
    while executing the search of the mass spectral database, monitoring a second elapsed search time of the second search and determining that the second elapsed search time exceeds the first maximum value, and
    upon identification of the second elapsed search time exceeding the first maximum value, terminating the second search.

13. Apparatus for analyzing a biological sample, comprising:
a separation device configured to temporally separate the biological sample into components;
an ionization source configured to receive a component of the biological sample and generate peptide ions from the component during an introduction period;
a fragmentation device configured to fragment the peptide ions to form product ions;
a mass analyzer configured to analyze the product ions to produce a product ion spectrum; and
a controller programmed with instructions for:
    executing a search of a mass spectral database to attempt to identify a candidate peptide in the mass spectral database that matches the product ion spectrum, the mass spectral database containing product mass spectral information for candidate peptides,
    while executing the search of the mass spectral database, monitoring an elapsed search time,
    upon identification of the candidate peptide that matches the product ion spectrum prior to the elapsed search time reaching a first maximum value that is shorter than the introduction period, causing the mass spectrometer to perform an action based on the identification, and
    terminating the search when the elapsed search time reaches the first maximum value.

14. The apparatus of claim 13, wherein the separation device is a chromatography device, and wherein the introduction period is defined by a chromatographic elution peak width of the component.

15. The apparatus of claim 13, wherein the first maximum value is: (i) defined by a user, or (ii) defined based on a history of search results for candidate peptides not being identified before the corresponding elapsed search times reached a second maximum value, the second maximum value less than the first maximum value.

16. The apparatus of claim 13, wherein the first maximum value is less than or equal to 20 milliseconds (ms).

17. The apparatus of claim 13, the candidate peptide is identified using amino acid sequences stored in the mass spectral database.

18. The apparatus of claim 13, wherein the candidate peptide is identified using empirically determined mass spectra stored in the mass spectral database.

19. The apparatus of claim 13, wherein the action to be performed based on the identification of the candidate peptide includes performing an additional stage of MSn analysis for one or more of the product ion species.

20. The apparatus of claim 13, wherein the action to be performed based on the identification of the candidate peptide includes refraining from performing an additional stage of MSn analysis for one or more of the product ion species.

21. The apparatus of claim 13, wherein the action to be performed based on the identification of the candidate peptide includes adjusting a fragmentation technique implemented by the fragmentation device used to fragment the peptide ions from a first fragmentation type to a second fragmentation type, the first fragmentation type and the second fragmentation type being different fragmentation types.

22. The apparatus of claim 13, wherein fragmentation is device configured to fragment the peptide ions to form second product ions, the mass analyzer is configured to analyze the second product ions to produce a second product ion spectrum, and the controller is further programmed with instructions for:
    executing a second search of the mass spectral database to attempt to identify a candidate peptide in the mass spectral database that matches the second product ion spectrum,
    while executing the search of the mass spectral database, monitoring a second elapsed search time of the second search and determining that the second elapsed search time exceeds the first maximum value, and
    upon identification of the second elapsed search time exceeding the first maximum value, terminating the second search.

23. An apparatus, comprising:
a mass analyzer configured to analyze product ions during an introduction period to produce a product ion spectrum; and
a controller programmed with instructions for:
    identifying a candidate peptide using the product ion spectrum and a database including information related to mass spectrums of candidate peptides;
    while executing the search of the database, monitoring an elapsed search time,
    comparing the elapsed search time with a maximum search time value that is shorter than the introduction period for performing the search of the database,
    upon identification of the candidate peptide prior to the elapsed search time reaching the maximum search time value, causing the mass spectrometer to perform an action based on the identification, and terminating the search when the elapsed search time reaches the first maximum value.

\* \* \* \* \*

UNITED STATES PATENT AND TRADEMARK OFFICE
CERTIFICATE OF CORRECTION

| | | |
|---|---|---|
| PATENT NO. | : 11,879,897 B2 | |
| APPLICATION NO. | : 16/426929 | |
| DATED | : January 23, 2024 | |
| INVENTOR(S) | : Derek J. Bailey | |

It is certified that error appears in the above-identified patent and that said Letters Patent is hereby corrected as shown below:

In the Claims

In Column 18, Claim 17, Line 13, delete "the candidate" and insert -- wherein the candidate --

In Column 18, Claim 23, Line 60, delete "peptides;" and insert -- peptides, --

Signed and Sealed this
Twenty-sixth Day of March, 2024

Katherine Kelly Vidal
*Director of the United States Patent and Trademark Office*